(12) United States Patent
Gao et al.

(10) Patent No.: US 12,133,848 B2
(45) Date of Patent: Nov. 5, 2024

(54) ORAL PRODUCT

(71) Applicant: Altria Client Services LLC, Richmond, VA (US)

(72) Inventors: Feng Gao, Midlothian, VA (US); Frank Scott Atchley, Midlothian, VA (US); Gregory James Griscik, Midlothian, VA (US); Christopher Joseph Dinovi, Ruther Glen, VA (US); Phillip M. Hulan, Midlothian, VA (US); Diane L. Gee, Chesterfield, VA (US); Jason Flora, Richmond, VA (US); Shuzhong Zhuang, Glen Allen, VA (US)

(73) Assignee: Altria Client Services LLC, Richmond, VA (US)

( * ) Notice: Subject to any disclaimer, the term of this patent is extended or adjusted under 35 U.S.C. 154(b) by 149 days.

(21) Appl. No.: 18/061,680

(22) Filed: Dec. 5, 2022

(65) Prior Publication Data

US 2023/0097809 A1    Mar. 30, 2023

Related U.S. Application Data (63) Continuation of application No. 16/942,014, filed on Jul. 29, 2020, now Pat. No. 11,517,566, which is a (Continued)

(51) Int. Cl.
*A24B 13/00* (2006.01)
*A24B 15/14* (2006.01)
(Continued)

(52) U.S. Cl.
CPC ............ *A61K 31/465* (2013.01); *A24B 15/14* (2013.01); *A24B 15/16* (2013.01); *A24B 15/30* (2013.01); *A24B 15/308* (2013.01); *A61J 3/10* (2013.01); *A61K 9/0053* (2013.01); *A61K 9/2013* (2013.01); *A61K 9/2031* (2013.01); *A61K 9/205* (2013.01); *A61K 9/2054* (2013.01);
(Continued)

(58) Field of Classification Search
None
See application file for complete search history.

(56) References Cited

U.S. PATENT DOCUMENTS

| | | | |
|---|---|---|---|
| 2,162,738 | A | 6/1939 | McCoy |
| 3,139,436 | A | 6/1964 | Bicking |

(Continued)

FOREIGN PATENT DOCUMENTS

| | | |
|---|---|---|
| CN | 103040090 A | 4/2013 |
| WO | WO-2013109961 A1 | 7/2013 |

OTHER PUBLICATIONS

International Search Report and Written Opinion in International Application No. PCT/US2014/037698, mailed Oct. 17, 2014, 12 pages.

(Continued)

*Primary Examiner* — Eric Yaary
(74) *Attorney, Agent, or Firm* — Harness, Dickey & Pierce, P.L.C.

(57) ABSTRACT

An oral product includes a body that is wholly receivable in an oral cavity. The body includes a mouth-stable polymer matrix, cellulosic fibers embedded in the mouth-stable polymer matrix, and a mouth-soluble binder dispersed in the mouth-stable polymer matrix.

20 Claims, 4 Drawing Sheets

Related U.S. Application Data continuation of application No. 16/214,490, filed on Dec. 10, 2018, now Pat. No. 10,780,085, which is a continuation of application No. 14/940,698, filed on Nov. 13, 2015, now Pat. No. 10,183,016, which is a continuation of application No. 14/274,916, filed on May 12, 2014, now Pat. No. 9,185,931.

(60) Provisional application No. 61/822,596, filed on May 13, 2013.

(51) Int. Cl.

| | |
|---|---|
| *A24B 15/16* | (2020.01) |
| *A24B 15/30* | (2006.01) |
| *A61J 3/10* | (2006.01) |
| *A61K 9/00* | (2006.01) |
| *A61K 9/20* | (2006.01) |
| *A61K 31/465* | (2006.01) |
| *A61K 36/81* | (2006.01) |
| *A61K 45/06* | (2006.01) |
| *B29C 48/00* | (2019.01) |
| *B29K 75/00* | (2006.01) |
| *B29K 401/00* | (2006.01) |
| *B29K 407/00* | (2006.01) |
| *B29L 31/00* | (2006.01) |

(52) U.S. Cl.
CPC .......... *A61K 9/2095* (2013.01); *A61K 36/81* (2013.01); *A61K 45/06* (2013.01); *B29C 48/0011* (2019.02); *B29C 48/0022* (2019.02); *B29C 48/022* (2019.02); *B29K 2075/00* (2013.01); *B29K 2401/00* (2013.01); *B29K 2407/00* (2013.01); *B29L 2031/753* (2013.01)

(56) References Cited

U.S. PATENT DOCUMENTS

| | | |
|---|---|---|
| 3,396,735 A | 8/1968 | Von Bethmann et al. |
| 4,153,063 A | 5/1979 | Roselius et al. |
| 4,448,208 A | 5/1984 | Friedrich et al. |
| 4,528,993 A | 7/1985 | Sensabaugh, Jr. et al. |
| 4,660,577 A | 4/1987 | Sensabaugh et al. |
| 4,848,373 A | 7/1989 | Lenkey |
| 5,372,149 A | 12/1994 | Roth et al. |
| 5,487,792 A | 1/1996 | King et al. |
| 2004/0118422 A1 | 6/2004 | Lundin et al. |
| 2004/0247669 A1 | 12/2004 | Gin et al. |
| 2005/0152971 A1 | 7/2005 | Rinker et al. |
| 2005/0178398 A1 | 8/2005 | Breslin et al. |
| 2006/0185684 A1 | 8/2006 | Albino et al. |
| 2006/0191548 A1 | 8/2006 | Strickland et al. |
| 2007/0186941 A1 | 8/2007 | Holton et al. |
| 2008/0209586 A1 | 8/2008 | Nielsen et al. |
| 2009/0065013 A1 | 3/2009 | Essen et al. |
| 2009/0293889 A1 | 12/2009 | Kumar et al. |
| 2010/0040679 A1 | 2/2010 | Chang et al. |
| 2010/0163062 A1 | 7/2010 | Atchley et al. |
| 2010/0300463 A1 | 12/2010 | Chen et al. |
| 2011/0139166 A1 | 6/2011 | Luzenberg, Jr. |
| 2011/0274628 A1 | 11/2011 | Borschke |
| 2012/0024301 A1 | 2/2012 | Carroll et al. |
| 2012/0031414 A1 | 2/2012 | Atchley et al. |
| 2012/0138073 A1 | 6/2012 | Cantrell et al. |
| 2013/0053603 A1 | 2/2013 | Norstrom et al. |
| 2013/0074855 A1 | 3/2013 | Holton, Jr. |
| 2013/0186416 A1 | 7/2013 | Gao et al. |

OTHER PUBLICATIONS

International Preliminary Report on Patentability in International Application No. PCT/US2014/037698, mailed Nov. 26, 2015, 9 pages.

Office Action from corresponding European application No. 14 730 029.7 dated Nov. 26, 2018.

European Office Action for corresponding Application No. 14730029. 7-1105, dated Jul. 2, 2020.

European Office Action for EP Application 14730029.7 dated Feb. 27, 2023 (7 pages).

ORAL PRODUCT

CROSS REFERENCE TO RELATED APPLICATIONS

This application is a continuation of U.S. application Ser. No. 16/942,014, filed Jul. 29, 2020, which is a continuation of U.S. application Ser. No. 16/214,490, filed Dec. 10, 2018, which is a continuation of U.S. patent application Ser. No. 14/940,698 filed Nov. 13, 2015, which is a continuation of and claims priority to U.S. patent application Ser. No. 14/274,916 filed May 12, 2014, which claims priority to U.S. Provisional Application Ser. No. 61/822,596 filed May 13, 2013, the entire contents of each of which are incorporated herein by reference.

TECHNICAL FIELD

This document relates to oral products including mouth-stable polymers and one or more additives.

BACKGROUND

Tobacco can be enjoyed by adult tobacco consumers in a variety of forms. Smoking tobacco is combusted and the aerosol either tasted or inhaled (e.g., in a cigarette, cigar, or pipe). Smokeless tobacco products are not combusted and include: chewing tobacco, moist smokeless tobacco, snus, and dry snuff. Chewing tobacco is coarsely divided tobacco leaf that is typically packaged in a large pouch-like package and used in a plug or twist. Moist smokeless tobacco is a moist, more finely divided tobacco that is provided in loose form or in pouch form and is typically packaged in round cans and used as a pinch or in a pouch placed between an adult tobacco consumer's cheek and gum. Snus is a heat treated smokeless tobacco. Dry snuff is finely ground tobacco that is placed in the mouth or used nasally.

A growing number of governments are now implementing restrictions on smoking in public places, such as restaurants and transport facilities. In some countries, such as the United States, some workplaces are also covered by public restrictions. Smokeless products may also be banned by certain governments or workplaces.

Trans-buccal systems such as nicotine-containing chewing gum as well as transdermal nicotine delivery systems are well known in the art. These systems, however, do not consistently provide a suitable tobacco-like experience for some adult tobacco consumers.

Oral products providing flavor and/or one or more active ingredients are also known. One such oral product is chewing gum. Other oral products include hard candies (e.g., mints). Softer gelatin-based oral products are also known. Pharmaceutical and therapeutic products (e.g., cough-suppressant lozenges) can also be provided in a solid form for oral consumption. The flavor release and/or active agent release characteristics for an oral product are important for providing an improved consumer product.

SUMMARY

This specification describes an oral product that includes a mouth-stable polymer matrix, cellulosic fibers, and one or more mouth-soluble binders. The oral product can provide a satisfying tactile and/or flavor experience. The oral product can include one or more additives, such as an active ingredient, a flavorant, a sweetener, or a combination thereof. In some cases, the cellulosic fibers can include natural active ingredients and/or flavors. In particular embodiments, the oral product can provide an extended additive/active/flavor release time. The oral product includes a body that is at least partially receivable in an oral cavity of an adult consumer. In some embodiments, a body includes a mouth-stable polymer matrix, cellulosic fibers embedded in the stable polymer matrix, and the binder dispersed within the body.

The mouth-soluble binder can be a carbohydrate, protein, or combinations thereof. In some embodiments, the mouth-soluble binder includes a hydroxyl containing compound, a dextrin or dextrin derivative, carboxymethyl cellulose, hydroxypropyl cellulose, hydroxyethyl cellulose, hydroxypropyl methyl cellulose, methyl cellulose, konjac, collagen, inulin, soy protein, whey protein, casein, wheat gluten, carrageenan, alginates, propylene glycol alginate, xanthan, dextrin, pullulan, curdlan, gellan, locust bean gum, guar gum, tara gum, gum tragacanth, pectin, agar, zein, karaya, gelatin, psyllium seed, chitin, chitosan, gum acacia, polyvinyl pyrrolidone, polyethylene oxide, polyvinyl alcohol, pectin, or a combination thereof. In certain embodiments, the mouth-soluble binder is selected from the group of guar gum, xanthan, cellulose, and combinations thereof. For example, oral products can include between 0.05 and 1.0 weight percent of a binder that includes guar gum, xanthan, and carboxymethyl cellulose. In some cases, oral products provided herein can include between 0.2 weight percent and 0.5 weight percent binder. The binder can provide the oral product with a modified texture and flavor release profile. The oral product, according to certain embodiments, includes nicotine or a derivative thereof. The oral product can provide a tobacco-like flavor experience and favorable tactile experience. Combinations of additives (e.g., sweeteners, flavorants, and nicotine) can be combined to provide a favorable tactile and flavor experience.

The oral product, according to certain embodiments, includes flavorants, sweeteners, vitamins, minerals, therapeutic agents, nutraceuticals, energizing agents, soothing agents, coloring agents, amino acids, chemsthetic agents, antioxidants, food grade emulsifiers, pH modifiers, botanicals, teeth whitening agents, and/or alkaloids (e.g., caffeine). In some cases, the oral product can be substantially free of tobacco. Combinations of additives (e.g., sweeteners, flavorants, and caffeine) can be combined to provide a favorable tactile and flavor experience.

In some cases, the cellulosic fibers can be tobacco fibers. An oral product including tobacco fibers can include a body that is at least partially receivable in an oral cavity of an adult tobacco consumer. In some embodiments, the body includes a mouth-stable polymer matrix, tobacco fibers embedded in the stable polymer matrix, and a binder dispersed in the body. The tobacco fibers dispersed in the body can provide an adult tobacco consumer a satisfying tactile and/or flavor experience. In some embodiments, an oral product can include exhausted-tobacco fibers and one or more additives.

These and other embodiments can each optionally include one or more of the following features. In some embodiments, the oral product's body includes at least 10 weight percent of the mouth-stable polymer. The mouth-stable polymer matrix can include polyurethane, silicon polymer, polyester, polyacrylate, polyethylene, poly(styrene-ethylene-butylene-styrene) ("SEBS"), poly(styrene-butadiene-styrene) ("SBS"), poly(styrene-isoprene-styrene)("SIS"), and other similar thermoplastic elastomers, or any copolymer, mixture, or combination thereof. The oral product can also include a plasticizer dispersed in the mouth-stable polymer matrix. For example, the plasticizer can be propylene glycol, glycerin, vegetable oil, triglycerides, or a combination thereof. The oral product can also include a sweetener and/or sugar alcohols dispersed in the body. The sweetener can be saccharine, sucralose, aspartame, acesulfame potassium, or a combination thereof. In some cases, an oral product can include one or more sugar alcohols selected from the group of sorbitol, xylitol, mannitol, maltitol, isomalt, and erythritol or combinations thereof.

The oral product, according to certain embodiments, is substantially free of tobacco plant tissue. Nicotine added to the oral product can be either synthetic or derived from tobacco. In some embodiments, the oral product includes between 0.1 mg and 6 mg nicotine. The oral products can also include an additive selected from the group consisting of minerals, vitamins, dietary supplements, nutraceuticals, energizing agents, soothing agents, amino acids, chemsthetic agents, antioxidants, botanicals, teeth whitening agents, therapeutic agents, or a combination thereof. The nicotine and/or other additives can be absorbed into the cellulosic fibers and polymer matrix. The oral product, according to some embodiments, includes exhausted-tobacco fibers as the cellulosic fibers. In some embodiments, the oral product includes tobacco fibers.

The oral product's body can have at least 10 weight percent cellulosic fibers. The cellulosic fibers can be derived from plant tissue. In some embodiments, the cellulosic fibers includes cellulose. The cellulosic fibers can further include lignin and/or lipids. The cellulosic fibers can be non-tobacco cellulosic fibers. For example, the cellulosic fibers can be selected from the following: sugar beet fiber, wood pulp fiber, cotton fiber, bran fiber, citrus pulp fiber, grass fiber, willow fiber, poplar fiber, and combinations thereof. The cellulosic fibers may also be chemically treated prior to use. For example, the cellulosic fibers can be CMC, HPMC, HPC, or other treated cellulosic material.

The oral product can include flavorants. The flavorants can be natural or artificial. Flavorants can be selected from the following: licorice, wintergreen, cherry and berry type flavorants, Drambuie, bourbon, scotch, whiskey, spearmint, peppermint, lavender, cinnamon, cardamon, apium graveolents, clove, cascarilla, nutmeg, sandalwood, bergamot, geranium, honey essence, rose oil, vanilla, lemon oil, orange oil, Japanese mint, cassia, caraway, cognac, jasmin, chamomile, menthol, ylang ylang, sage, fennel, pimenta, ginger, anise, coriander, coffee, mint oils from a species of the genus Mentha, cocoa, and combinations thereof. Synthetic flavorants can also be used. In certain embodiments, a combination of flavorants can be combined to imitate a tobacco flavor. The particular combination of flavorants can be selected from the flavorants that are generally recognized as safe ("GRAS"). Flavorants can also be included in the oral product as encapsulated flavorants.

The body of the oral product can have a variety of different shapes, some of which include disk, shield, rectangle, square, triangle, oval, or another appropriate shape. In some cases, the oral product has rounded corners to enhance mouth feel. According to certain embodiments, the body can have a length or width of between 5 mm and 25 mm and a thickness of between 1 mm and 10 mm.

The oral product's body can be compressible and springy. In some embodiments, the body has a compressibility @ 250 N of less than 95%, or less than 90%. In some embodiments, the body has a compressibility of @ 250 N of between 45% and 95%. The oral product's body can have a compressibility @ 425 N of less than 99%. For example, the body can have a compressibility @ 425 N of between 60% and 98%. The body can also have a percentage of springiness of at least 20%, at least 30%, at least 40%, at least 50%, at least 60%, at least 70%, at least 75%, or at least 80%. For example, the body can have a percentage of springiness of between 75% and −95%.

The oral product can also include an antioxidant. In some embodiments, the oral product includes between 0.01 weight percent and 5.0 weight percent antioxidant. Suitable antioxidants include ascorbyl palmitate, BHT, ascorbic acid, sodium ascorbate, monosterol citrate, tocopherols, propyl gallate, tertiary butylhydroquinone (TBHQ), butylated hydroxyanisole (BHA), Vitamin E, and derivatives thereof. The combination of antioxidant and nicotine can reduce the formation of nicotine-N-oxide.

The oral product can include a combination of soluble fibers and insoluble cellulosic fibers. In some embodiments, a ratio of soluble fiber to cellulosic fibers can be between 1:60 and 60:1. In some embodiments, the soluble fibers can include maltodextrin. In some embodiments, the soluble fibers comprise starch. The soluble fibers can be derived from corn. In general, another aspect of the subject matter described in this specification is methods of making and using the oral product. The methods of making the oral product can include the actions of extruding a mouth-stable polymer having cellulosic fibers and/or one or more additives dispersed therein.

The details of one or more embodiments of the subject matter described in this specification are set forth in the accompanying drawings and the description below. Other features, aspects, and advantages of the subject matter will become apparent from the description, the drawings, and the claims.

DETAILED DESCRIPTION

The oral products described herein include a mouth-stable polymer matrix, cellulosic fibers, and one or more mouth-soluble binders. In some cases, the oral products can include one or more additives can be dispersed in the mouth-stable polymer matrix such that the one or more additives are released from the oral product when the oral product is received within the oral cavity and exposed to saliva. The oral products described herein can provide a favorable additive release profile and tactile experience.

Suitable mouth-stable polymers include thermoplastic elastomers such as polyurethane. As used here, the term "mouth stable" means that the polymer does not appreciably dissolve or disintegrate when exposed to saliva within an oral cavity and at the normal human body temperature (e.g., about 98.6° F.) over a period of one hour. In addition to biostable polymers, mouth-stable polymers can include biodegradable polymers that breakdown over periods of days, weeks, months, and/or years, but do not appreciably break down when held in an oral cavity and exposed to saliva for a period of one hour. In some embodiments, the mouth-stable polymer is stable within an oral cavity and exposed to saliva at the normal human body temperature for a period of at least 6 hours, at least 12 hours, at least 24 hours, or at least 2 days. Accordingly, the oral products described herein can remain intact when placed within an oral cavity during a use period. After use, the mouth-stable polymer matrix can be removed from the oral cavity and discarded.

The mouth-stable polymer can have shape stability. In some cases, the oral product 110 can be chewed without significant and instantaneous permanent plastic deformation. As the oral product 100 is chewed, it can become more pliable and additional additives can become available for release into the oral cavity. Some embodiments of the oral product 110 can be adapted to remain non-sticky during and after use. After prolonged use, certain embodiments of the oral product 110 will expand and become flatter. The oral product, however, can retain the essence of its original shape.

One or more additives are included in the oral product and adapted to be released from the oral product when the oral product is placed in an oral cavity. The oral product, in some embodiments, includes nicotine. The oral product can include a combination of nicotine, sweeteners, and flavorants to mimic the flavor profile and tactile experience of certain tobacco products (e.g., a pouched smokeless tobacco product).

In some embodiments, a nicotine-containing oral product can be substantially free of tobacco plant tissue. As used herein, the term "tobacco plant tissue" refers to processed or non-processed cellulosic parts (e.g., leaves, stems) of a member of the genus *Nicotiana*, but does not include extracts of tobacco (e.g., tobacco-derived nicotine). For example, an oral product can include one or more organoleptic components extracted from raw or processed tobacco, yet be substantially free of tobacco plant tissue.

In addition to additives, sweeteners, and flavorants, the oral product can also include fibers, fillers, plasticizers, and/or processing aids. Fibers can help provide access to the additives, sweeteners, and/or flavorants. As will be discussed below, fibers can provide channels for additives, sweeteners, and/or flavorants to leach out of the mouth-stable polymer matrix. The fiber-polymer-binder composite can absorb one or more additives and provide a pathway for one or more additives to be released from the oral product. The fiber-polymer-binder composite can be porous. In some embodiments, the fiber-polymer-binder composite can have a plurality of pores having a pore diameter of between 40 microns and 60 microns and a plurality of pores having a pore diameter of between 1 micron and 10 microns. During use, saliva can be absorbed into the fiber-polymer-binder composite to release the additives, sweeteners, and/or flavorants. The absorbed saliva can enter the pores and/or cause the fibers to expand, which can facilitate further release of additives, sweeteners, and/or flavorants. Mechanical action (e.g., chewing) of the oral product can facilitate the release of the additives, sweeteners, and/or flavorants.

Fillers can also be included in the mouth-stable polymer matrix to alter the texture or pliability of the oral product. The mouth-stable polymer matrix can also include plasticizers, which can increase the softness of the oral product. Processing aids can also be present in the oral product and be used to facilitate shaping processes.

Oral Product Shapes and Packaging

Figure 1:
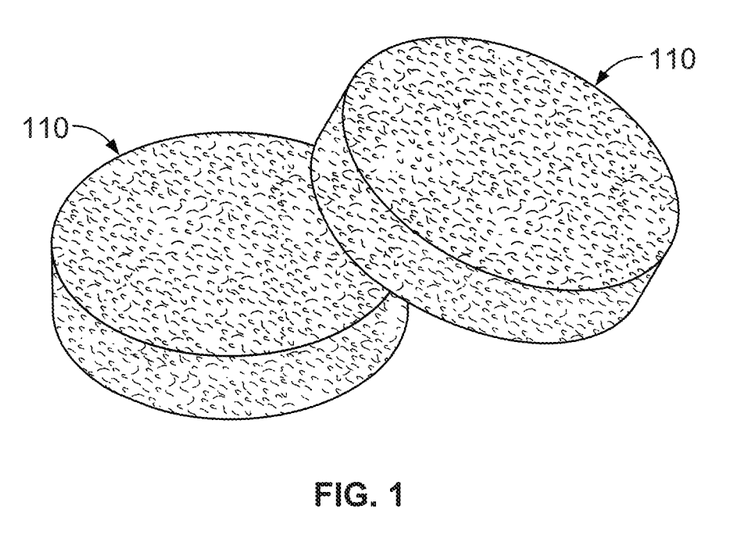
FIG. 1 is a perspective view of a pair of oral products.

FIG. 1 depicts an example of an oral product 110. The oral product 110 has a disk shape. For example, the oral product 110 can have a diameter of about 12 mm and a thickness of about 2.5 mm.

Figure 2A:
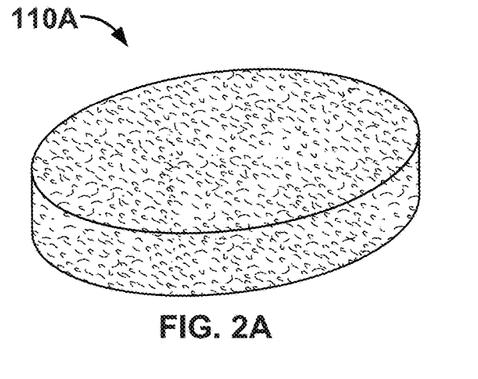
FIGS. 2A-2O illustrate various exemplary shapes of oral products.
Figure 2B:
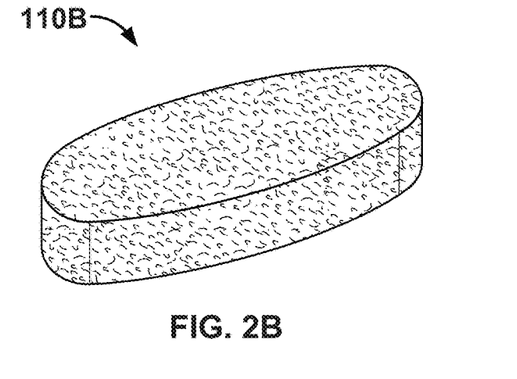
Figure 2C:
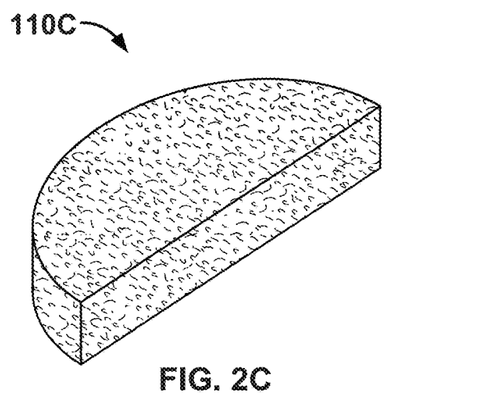
Figure 2D:
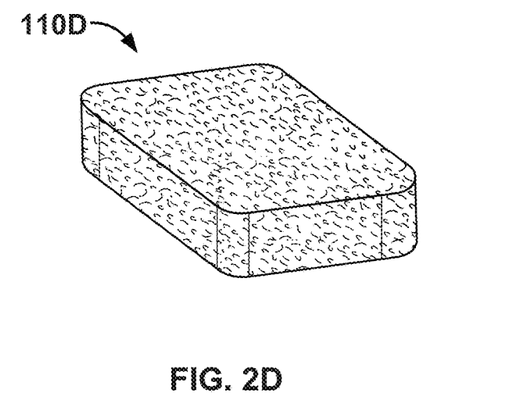
Figure 2E:
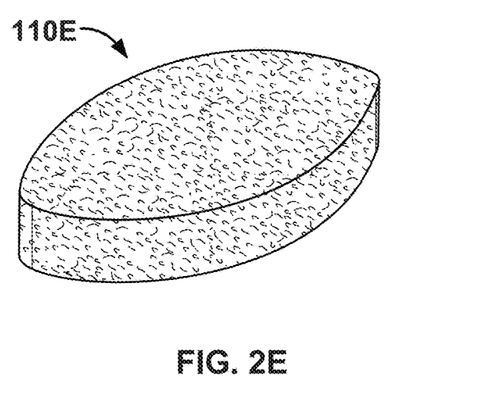
Figure 2F:
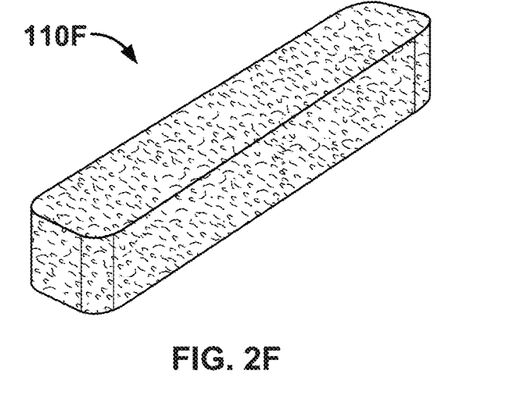
Figure 2G:
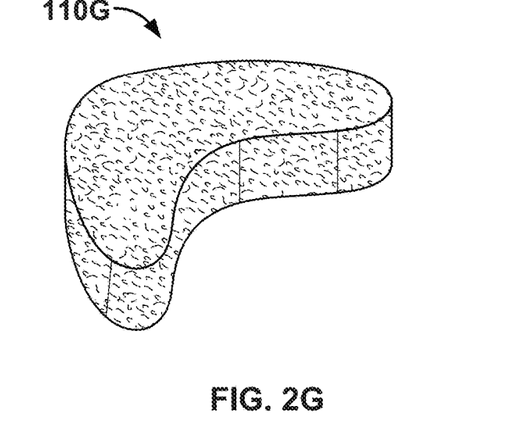
Figure 2H:
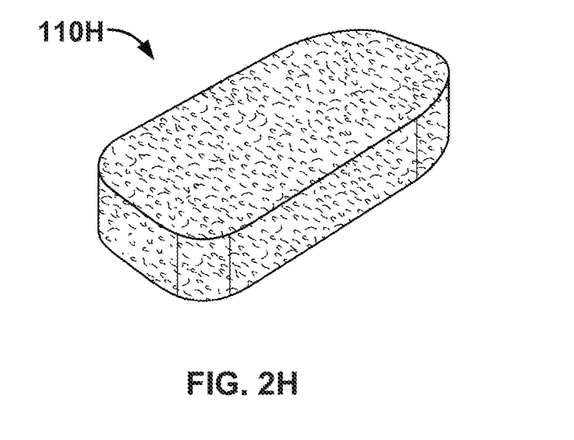
Figure 2I:
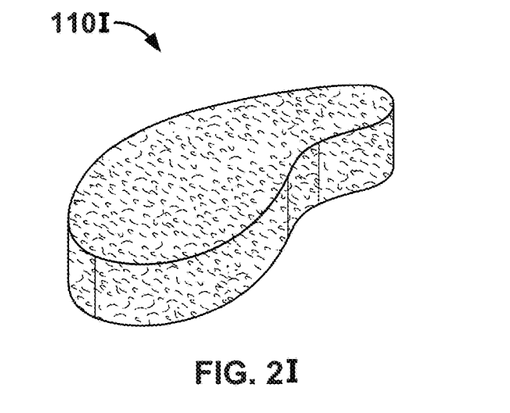
Figure 2J:
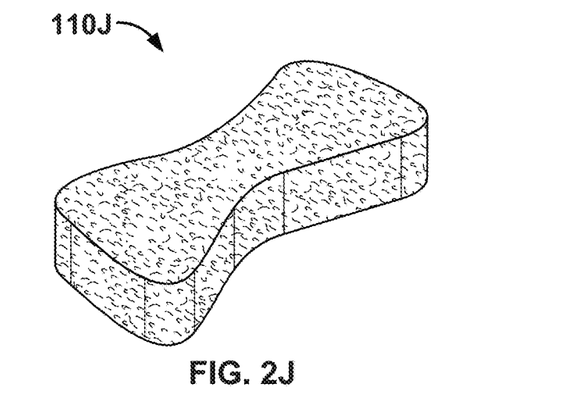
Figure 2K:
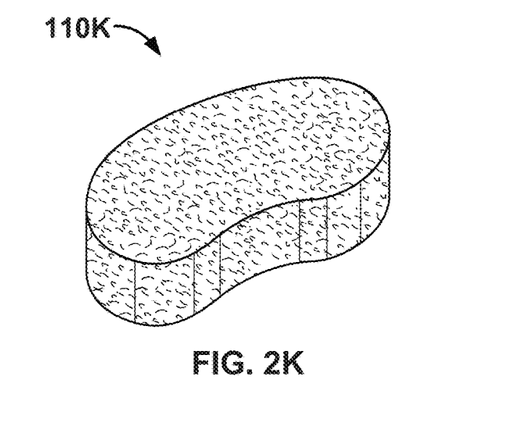
Figure 2L:
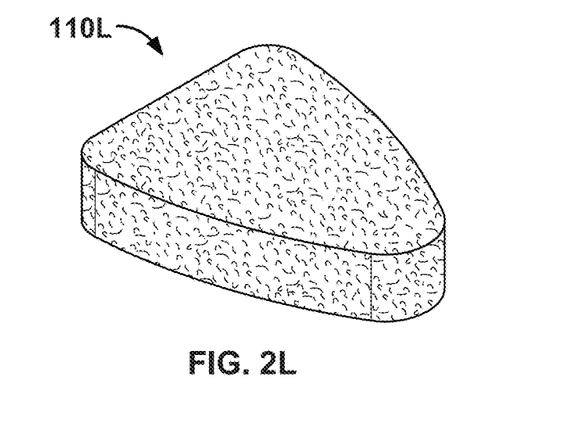
Figure 2M:
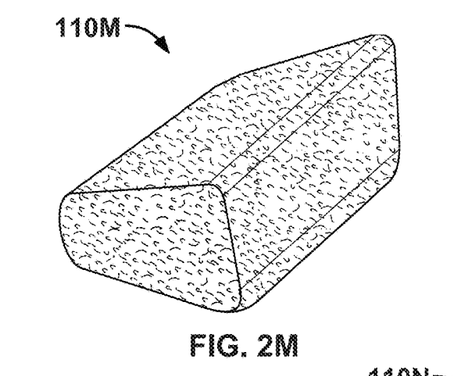
Figure 2N:
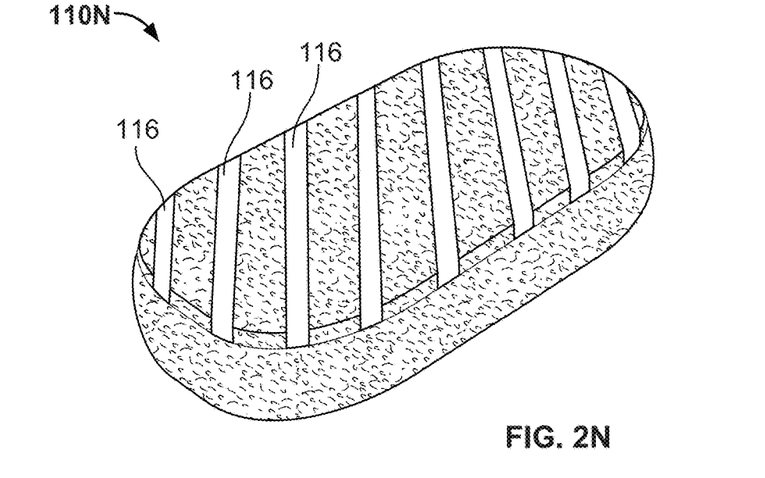

Referring now to FIGS. 2A-2N, the oral product 110 can be molded into any desired shape. For example, referring to FIGS. 2A-2L, the oral product 110A-L can be formed in a shape that promotes improved oral positioning in the oral cavity, improved packaging characteristics, or both. In some circumstances, the oral product 110A-L can be configured to be: (A) an elliptical-shaped oral product 110A; (B) an elongated elliptical-shaped oral product 110B; (C) semi-circular oral product 110C; (D) square or rectangular-shaped oral product 110D; (E) football-shaped oral product 110E; (F) elongated rectangular-shaped oral product 110F; (G) boomerang-shaped oral product 110G; (H) rounded-edge rectangular-shaped oral product 110H; (I) teardrop- or comma-shaped oral product 110I; (J) bowtie-shaped oral product 110J; (K) peanut-shaped oral product 110K; and (L) shield-shaped oral product. Alternatively, the oral product can have different thicknesses or dimensionality, such that a beveled article (e.g., a wedge) is produced (see, for example, product 110M depicted in FIG. 2M) or a hemi-spherical shape is produced. In some embodiments, the oral product has a shield shape.

In addition or in the alternative to flavorants being included within the mouth-stable polymer matrix, flavorants can be included on an exterior of the oral product 110. For example, referring to FIG. 2N some embodiments of an oral product 110N can be equipped with flavor strips 116.

Figure 2O:
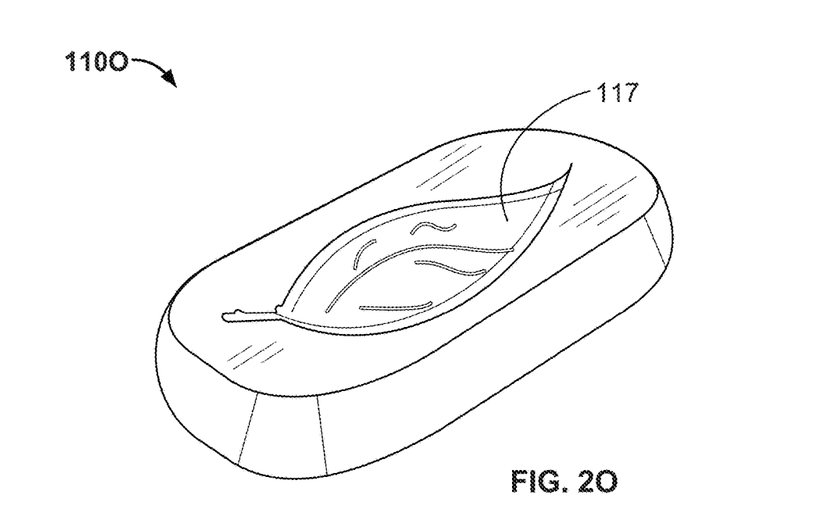

Referring to FIG. 2O, particular embodiments of the oral product 110 can be embossed or stamped with a design (e.g., a logo, an image, or the like). For example, the oral product 110O can be embossed or stamped with any type of design 117 including, but not limited to, a trademark, a product name, or any type of image. The design 117 can be formed directly into the oral product, arranged along the exterior of the product 110O. The design 117 can also be embossed or stamped into those embodiments with a dissolvable film 116 applied thereto.

In some embodiments, the oral product 110 or products 110A-O can be wrapped or coated in an edible or dissolvable film, which may be opaque, substantially transparent, or translucent. The dissolvable film can readily dissipate when the oral product 110 is placed in an oral cavity. In some embodiments, the oral product 110 can be coated with a mouth-stable material. Exemplary coating materials include Beeswax, gelatin, acetylated monoglyceride, starch (e.g., native potato starch, high amylose starch, hydroxypropylated potato starch), Zein, Shellac, ethyl cellulose, methylcellulose, hydroxypropyl methylcellulose, carboxymethyl cellulose, and combinations thereof. For example, a coating can include a combination of gelatin and methylcellulose. For example, coatings can include sugar alcohols, such as sorbitol, xylitol, mannitol, maltitol, isomalt, erythritol, maltodextrin, and/or polysaccharides. In some embodiments, a coating material can include a plasticizer. In some case, a coating can include a colorant, a flavorant, and/or a one or more of the additives discussed above. For example, a coating can include nicotine to provide a user with an initial nicotine burst. In some cases, the matrix of mouth-stable polymer 120 can have surfaces roughened to improve the adherence of a coating. In some cases, a coating can provide a glossy or semi-glossy appearance, a smooth surface, and/or an appealing visual aesthetic (e.g., a nice color). In some embodiments, the coating (e.g., a beeswax, Zein, acetylated monoglyceride, and/or hydroxypropylated potato starch coating) can provide soft mouth feel. In some embodiments, the coating (e.g., a methylcellulose, hydroxypropyl methylcellulose, carboxymethyl cellulose, ethyl cellulose, and/or gelatin coating) can provide a hard outer coating.

One or more oral products 110 can be packaged in a variety of conventional and non-conventional manners. For example, a plurality of oral products 110 can be packaged in a container having a lid. In other embodiments, a plurality of oral products 110 can be stacked and packaged in a paper, plastic, and/or aluminum foil tube. The packaging can have a child-resistant lid.

The oral product 110 can also include additional elements. In some embodiments, a mouth-stable polymer matrix including nicotine or a derivative thereof can be attached to a rod, tube, or stick.

Oral Product Properties

The oral product 110 can provide a favorable tactile experience (e.g., mouth feel). The oral product 110 can also retain its shape during processing, shipping, handling, and optionally use. As noted above, the oral product 110 includes a mouth-stable polymer matrix that does not appreciably dissolve or disintegrate when placed in an oral cavity and exposed to saliva. The mouth-soluble binder, however, can dissolve slowly to modify the flavor release profile and textural attributes of the oral product. The oral product 110 can have an elasticity allowing an adult consumer to work the product within the mouth. In some embodiments, the oral product 110 has at least some shape memory and thus can return to shape after being squeezed between teeth in an oral cavity. Working of the oral product 110 within the oral cavity can accelerate the release of the additives, sweeteners, and/or flavorants within the mouth-stable polymer matrix.

During use, the oral product 110 can absorb saliva into the polymer-fiber-binder matrix. The saliva can cause the polymer-fiber-binder matrix to swell, which can further increase access to different sections of the polymer-fiber matrix. The mouth-soluble binder can provide a modified flavor release provide that slowly dissolves to gradually increase access to additives, sweeteners, and/or flavorants within the mouth-stable polymer matrix. Physical activity, such as chewing of the product in the mouth, can also accelerate the polymer-matrix swelling and therefore the release of additives. As the product is chewed, saliva can access different sections of the polymer-fiber-binder matrix. The mouth-stable polymer can have shape stability. In some cases, the oral product 110 can be chewed without significant and instantaneous permanent plastic deformation (such as that experienced by a chewing gum when chewed). As the oral product 100 is chewed, it can become more pliable and additional additives can become available for release into the oral cavity. Some embodiments of the oral product 110 can be adapted to remain non-sticky during and after use. After prolonged use, certain embodiments of the oral product 110 will expand and become flatter. The oral product, however, can retain the essence of its original shape. The amount of deformation will depend on the duration of use and an amount of mouth force used. As the product is used, it can increase in both weight and volume, due to the swelling. With greater the physical manipulation, the oral product 110 will have a greater amount of swelling and thus have a larger weight gain. In certain embodiments, the oral product 110 will have an increase in weight of between 4 and 75 percent when chewed by an adult consumer for 30 minutes.

One way of characterizing the properties of the oral product is by measuring the compressibility and springiness of the product. The compressibility can be calculated as a percentage of reduction in thickness of the sample when the sample is compressed with a standardized probe with a particular force. As used herein, the term "compression @ 250 N test" defines a test of a sample where the sample is placed on a flat stationary surface and twice compressed with a 10 mm-diameter-sphere-tipped probe with a force of 250 N with a hold time of 30 seconds between compressions. The "percentage of compression @ 250 N" is the maximum amount of reduction in thickness of the sample during the compression @250 N test. For example, if a 3 mm thick sample is compressed to a minimum thickness of 1.5 mm during either of the two compressions, the sample is said to have a 50% compression @ 250 N. As used herein, the term "compression @ 425 N test" defines a test of a sample where the sample is placed on a flat stationary surface and twice compressed with a 10 mm-diameter-sphere-tipped probe with a force of 425 N with a hold time of 30 seconds between compressions. For comparison, a normal human bite force is typically between 400 and 500 N.

In some embodiments, the oral product 110 has a percentage of compression @ 250 N of less than 95%. In certain embodiments, the oral product 110 has a percentage of compression @ 250 N of less than 90%. In certain embodiments, the oral product 110 has a percentage of compression @ 250 N of at least 10%, at least 25%, at least 40%, at least 60%, at least 70%, at least 80%, or at least 90%. For example, the oral product can have a percentage of compression @ 250 N of between 80% and 90%. In some embodiments, the oral product 110 has a percentage of compression @ 425 N of less than 99%. In certain embodiments, the oral product 110 has a percentage of compression @ 425 N of less than 98%, less than 97%, or less than 96%. In certain embodiments, the oral product 110 has a percentage of compression @ 425 N of at least 10%, at least 25%, at least 50%, or at least 60%. For example, the oral product can have a percentage of compression @ 425 N of between 65% and 98%. FIG. 9A, discussed in more detail below, depicts examples of compression test results for certain embodiments of oral products, for gum (both chewed and fresh), and for an eraser.

The springiness of a sample can be measured by measuring the percentage of recovery after a sample is compressed. As used herein, the term "percentage of springiness" means the percentage of thickness recovery of the sample during a 30 second recovery time after being compressed by the compression @ 425 N test using the 10 mm-diameter-sphere-tipped probe. For example, if a sample is compressed from an original thickness of 3.0 mm to a thickness of 2.0 mm and then recovers to 2.5 mm after 30 seconds, the springiness of the sample would be 50%. In some embodiments, the oral product 110 has a percentage of springiness of at least 20%. In certain embodiments, the oral product 110 has a percentage of springiness of at least 40%, at least 50%, at least 60%, at least 70%, at least 75%, at least 80%, or at least 90%. In certain embodiments, the percentage of springiness is less than 95%, less than 90%. For example, the oral product can have a percentage of springiness of between 75% and 95%. In some cases, oral products can have a compression @250N that ranges from 80% to 90%, a compression @425N that ranges from 90% to 99%, and/or a springiness that ranges from 80% to The particular materials used in the oral product 110 and the processing techniques discussed below can have an impact on the compressibility and springiness of the oral product. In addition to different materials have different compressibility and springiness properties, the incorporation of air bubbles or channels, or different fillers and/or fibers can also have an impact on the elasticity and pliability of the oral product. Additionally, the material properties of the overall oral product 110 can change as additives are released. In some embodiments, fibers and/or fillers can also dissolve or disintegrate during use and thus alter the material properties of the oral product 110 during use.

The oral product 110 can have a variety of colors. In some embodiments, the oral product 110 has an off-white color. In other embodiments, natural and artificial coloring can be added to the mouth-stable polymer before or during the molding process to form oral products 110 having a predetermined color. Encapsulated flavors can be added during the extrusion process to create speckles, patterns or dots within the oral product.

Polymers

The mouth-stable polymer can be a variety of different biocompatible and biostable polymers. In some cases, a mouth-stable polymer matrix can include a single type of polymer (e.g., polyurethane). In some cases, a mouth-stable polymer matrix can include a blend of different polymers. In some embodiments, the mouth-stable polymer is a polymer generally recognized as safe by an appropriate regulatory agency. In some embodiments, the polymer is a thermoplastic polymer. The polymer can also be a thermoplastic elastomer. For example, suitable mouth-stable polymers include polyurethanes, silicon polymers, polyesters, polyacrylates, polyethylenes, polypropylenes, polyetheramides, polystyrenes (e.g., acrylonitrile butadiene styrene, high impact polystyrenes (HIPS)) polyvinyl alcohols, polyvinyl acetates, polyvinyl chlorides, polybutyl acetates, butyl rubbers (e.g., polyisobutylenes), SEBS, SBS, SIS, and mixtures and copolymers thereof. Many suitable mouth-stable polymers exhibit undetectable dissolution or disintegration when held in the mouth for one hour. However, biocompatible, biodegradable polymers that exhibit less 25% dissolution or disintegration when held in the mouth for one hour, 6 hours, 12 hours, 24 hours, or 48 hours are also suitable for use as mouth-stable polymers in an oral product. In certain embodiments, the mouth-stable polymer is food-grade or medical-grade polymers (e.g., medical-grade polyurethane).

The mouth-stable polymer forms the mouth-stable polymer matrix of the oral product 110. In some embodiments, the oral product includes at least 10 weight percent of one or more mouth-stable polymers. In certain embodiments, the oral product includes at least 20 weight percent, at least 30 weight percent, at least 40 weight percent, at least 50 weight percent, at least 60 weight percent, at least 70 weight percent, at least 80 weight percent, or at least 90 weight percent of one or more mouth-stable polymers. In certain embodiments, the oral product includes between 10 and 90 weight percent of one or more mouth-stable polymers. Accordingly to some embodiments, the oral product includes between 40 and 80 weight percent of the mouth-stable polymers. Some embodiments of the oral product have between 55 and 70 weight percent polymers.

The mouth-stable polymer according to certain embodiments has a flexural modulus of at least 5 MPa when tested according to ASTM Testing Method D790 or ISO 178 at 23 degrees Celsius. In some embodiments, the flexural modulus is at least 10 MPa. For example, the flexural modulus can be between 10 MPa and 30 MPa. In some embodiments, the mouth-stable polymer is a grade that complies with food-contact regulations applicable in one or more countries (e.g., US FDA regulations). In some embodiments, the mouth-stable polymer can be a polyurethane, SIS, or other thermal plastic elastomer meeting the requirements of the FDA-modified ISO 10993, Part 1 "Biological Evaluation of Medical Devices" tests with human tissue contact time of 30 days or less. The mouth-stable polymer can have a shore Hardness of 50D or softer, a melt flow index of 3 g/10 min at 200° C./10 kg, a tensile strength of 10 MPa or more (using ISO 37), and a ultimate elongation of less than 100% (using ISO 37).

Cellulosic Fibers

The oral product can include cellulosic fibers within the mouth-stable polymer matrix. As will be discussed below, the cellulosic fibers can be mixed with the mouth-stable polymer and the mouth-soluble binder prior to or during an extrusion process. The cellulosic fibers can provide passages in the mouth-stable polymer matrix, which can permit certain additives within the mouth-stable polymer matrix to be released into an oral cavity when the oral product is received in an oral cavity and exposed to saliva. The additives can be absorbed or dispersed in fiber-polymer-binder composite and/or form pockets within the mouth-stable polymer matrix, which can be accessed via the fibers 130.

The cellulosic fibers can be obtained by processing plant tissue. Suitable sources for cellulosic fibers include wood pulp, cotton, sugar beets, bran, citrus pulp fiber, switch grass and other grasses, Salix (willow), tea, opulus (poplar), or combinations thereof. The cellulosic fibers may also be chemically treated prior to use. For example, the cellulosic fibers can be CMC, HPMC, HPC, or other treated cellulosic material. In some embodiments, the cellulosic fibers can be chopped or shredded plant tissue and, as such, contain various compounds naturally present in the tissue in addition to cellulosic fibers, e.g., lignin, lipids, or flavor compounds. In some embodiments, the cellulosic fibers can be chopped or shredded plant tissue comprising various natural flavors, sweeteners, or active ingredients. In some embodiments, the oral product 110 can include nicotine as an additive (optionally with additional sweeteners and flavors) and non-tobacco cellulosic fiber, and thus be substantially free of tobacco plant tissue.

The cellulosic fibers can have a variety of dimensions. The dimensions of the fibers (in addition to the amount) can impact the release characteristics of the additives. For example, cellulosic fibers can be hydrophilic, thus water soluble additives (e.g., nicotine) can preferentially be absorbed in fiber-polymer-binder composite. In certain embodiments, the cellulosic fiber can be processed to have an average fiber size of less than 200 micrometers. In particular embodiments, the fibers are between 75 and 125 micrometers. In other embodiments, the fibers are processed to have a size of 75 micrometers or less.

The oral product 110 can also include soluble fibers in addition to cellulosic fibers. The soluble fibers can be adapted to dissolve when exposed to saliva when the oral product 110 is received in an oral cavity. In some embodiments, the soluble fiber can be a maltodextrin. The maltodextrin can be derived from corn. For example, Soluble Dietary Fiber can be included in an oral product 110. Soluble fibers can be used alone or with cellulosic fibers to provide channels for additives to be released from the oral product 110. As the soluble fibers dissolve, the oral product 110 can become more flexible and the additional channels can open up to permit the release of additional additive deposits. Suitable soluble fibers include psyllium fibers. The ratio of soluble to insoluble fiber can impact the softness of texture of the oral product 110. The ratio of soluble to insoluble fiber can also impact the compressibility of the oral product 110. In some embodiments, a ratio of soluble to insoluble fiber is between 1:60 and 60:1. In some embodiments, the ratio of soluble to insoluble fiber is greater than 1:50, greater than 1:40, greater than 1:30, greater than 1:20, greater than 1:10, or greater than 1:5. In some embodiments, the ratio of soluble to insoluble fiber is less than 1:1, less than 1:2, less than 1:5, less than 1:10, less than 1:20, or less that 1:30. In some case, an oral product having a mixture of soluble and insoluble fibers can have a percentage of compression @ 250 N of between 60 percent and 98 percent, between 65 percent and 95 percent, between 70 percent and 90 percent, or between 80 and 89 percent. In some embodiments, the cellulosic fibers can be partially soluble. For example, sugar beet fibers can partially dissolve during use.

In some cases, an oral product can contain cellulosic fibers derived from tobacco. By "tobacco" it is meant a part, e.g., leaves, flowers, and stems, of a member of the genus *Nicotiana*. Exemplary species of tobacco include *N. rustica, N. tabacum, N. tomentosiformis*, and *N. sylvestris*. Suitable tobacco fibers can include tobacco fibers formed from fermented and unfermented tobaccos, dark air-cured, dark fire-cured, burley, flue cured, and cigar filler or wrapper, as well as the products from the whole leaf stemming operation. For example, tobacco can be conditioned by heating, sweating and/or pasteurizing steps as described in U.S. Publication Nos. 2004/0118422 or 2005/0178398. Fermenting typically is characterized by high initial moisture content, heat generation, and a 10 to 20% loss of dry weight. See e.g., U.S. Pat. Nos. 4,528,993; 4,660,577; 4,848,373; and 5,372,149. Cured, or cured and fermented tobacco can be further processed (e.g., cut, expanded, blended, milled or comminuted) prior to incorporation into the mouth-stable polymer matrix. The tobacco fibers, in some embodiments, include cured long cut fermented moist tobacco having an oven volatiles content of between 48 and 50 weight percent prior to mixing with the mouth-stable polymer, the mouth-soluble binder, and optionally flavorants and/or other additives.

The tobacco fibers can, in some embodiments, be prepared from or include leaf tobacco from tobacco plants having less than 20 μg of DVT per cm2 of green leaf tissue. For example, the tobacco can be selected from the tobaccos described in U.S. Patent Publication No. 2008/0209586, which is hereby incorporated by reference. Tobacco compositions containing tobacco from such low-DVT varieties exhibit improved flavor characteristics in sensory panel evaluations when compared to tobacco or tobacco compositions that do not have reduced levels of DVTs.

Mouth-Soluble Binder

Mouth-soluble binders suitable for use in the oral product described herein include orally compatible polymers, such as cellulosics (e.g., carboxymethyl cellulose (CMC), hydroxypropyl cellulose (HPC), hydroxyethyl cellulose (HEC), hydroxypropyl methyl cellulose (HPMC), and methyl cellulose (MC)); natural polymers (e.g., starches and modified starches, konjac, collagen, inulin, soy protein, whey protein, casein, and wheat gluten); seaweed-derived polymers (e.g., carrageenan (kappa, iota, and lambda); alginates, (and propylene glycol alginate), microbial-derived polymers (e.g., xanthan, dextrin, pullulan, curdlan, and gellan); extracts (e.g., locust bean gum, guar gum, tara gum, gum tragacanth, pectin (lo methoxy and amidated), agar, zein, karaya, gelatin, psyllium seed, chitin, and chitosan), exudates (e.g., gum acacia (arabic) and shellac), synthetic polymers (e.g., polyvinyl pyrrolidone, polyethylene oxide, and polyvinyl alcohol)), and pectin.

The mouth-soluble binder, in some embodiments, is guar gum, xanthan, cellulose, or a combination thereof. The cellulose can be carboxymethyl cellulose (CMC). Guar gum, xanthan, CMC, and some combinations thereof can be obtained from, for example, TIC Gums Inc., located in White Marsh, Maryland and at www.ticgums.com. Guar gum is sold by TIC Gums Inc. under the trade name GUARNT. Carboxymethyl cellulose (CMC) is sold by TIC Gums Inc. under the trade name TICALOSE. Xanthan is sold by TIC Gums Inc. under the trade name TICAXAN. TIC Gums Inc. also sells some mixed binders, such as the mixed binder systems sold under the trade names TICALOID and TICAFILM. In some embodiments, TICALOID LITE Powder is used as the binder in the oral products.

The mouth-soluble binder can be present in amounts that allow the oral product 110 to have the material properties described herein. The specific amount of mouth-soluble binder used to achieve the particular material properties can depend, in part, on the type of mouth-soluble binder used. In some embodiments, the oral products 110 include at least 0.1 weight percent mouth-soluble binder. The oral products 110 have, in some embodiments, less than 5.0 weight percent mouth-soluble binder. In some embodiments, the oral products 110 have between 0.0.01 and 2.0 weight percent mouth-soluble binder. In some embodiments, the oral products 110 have between 0.1 and 1 weight percent binder.

Additives

A variety of additives can be included in the oral product 110. The additives can include alkaloids (e.g., nicotine), minerals, vitamins, dietary supplements, nutraceuticals, energizing agents, soothing agents, coloring agents, amino acids, chemsthetic agent, antioxidants, food grade emulsifiers, pH modifiers, botanicals (e.g., green tea), teeth whitening (e.g., SHRIMP), therapeutic agents, sweeteners, flavorants, and combinations thereof. In certain embodiments, the additives include nicotine, sweeteners, and flavorants. With certain combinations of nicotine, sweeteners, and flavorants, the oral product may provide a flavor profile and tactile experience similar to certain tobacco products.

Nicotine

Nicotine within the oral product can be tobacco-derived nicotine, synthetic nicotine, or a combination thereof. In certain embodiments, the oral product includes between 0.1 mg and 6.0 mg of nicotine. In some of these embodiments, the oral product includes between 1.0 mg and 3.0 mg of nicotine.

Tobacco-derived nicotine can include one or more other tobacco organoleptic components other than nicotine. The tobacco-derived nicotine can be extracted from raw (e.g., green leaf) tobacco and/or processed tobacco. Processed tobaccos can include fermented and unfermented tobaccos, dark air-cured, dark fire cured, burley, flue cured, and cigar filler or wrapper, as well as the products from the whole leaf stemming operation. The tobacco can also be conditioned by heating, sweating and/or pasteurizing steps as described in U.S. Publication Nos. 2004/0118422 or 2005/0178398. Fermenting typically is characterized by high initial moisture content, heat generation, and a 10 to 20% loss of dry weight. See, e.g., U.S. Pat. Nos. 4,528,993; 4,660,577; 4,848,373; and 5,372,149. By processing the tobacco prior to extracting nicotine and other organoleptic components, the tobacco-derived nicotine may include ingredients that provide a favorable experience.

The tobacco-derived nicotine can be obtained by mixing cured and fermented tobacco with water or another solvent (e.g., ethanol) followed by removing the insoluble tobacco material. The tobacco extract may be further concentrated or purified. In some embodiments, select tobacco constituents can be removed. Nicotine can also be extracted from tobacco in the methods described in the following patents: U.S. Pat. Nos. 2,162,738; 3,139,436; 3,396,735; 4,153,063; 4,448, 208; and 5,487,792.

The nicotine can also be purchased from commercial sources, whether tobacco-derived or synthetic. In other embodiments, the oral product can include a derivative of nicotine (e.g., a salt of nicotine).

Antioxidants

The oral product 110 can also include one or more antioxidants. In some embodiments, an oral product 110 can include a combination of nicotine and antioxidants. Antioxidants can result in a significant reduction in the conversion of nicotine into nicotine-N-oxide when compared to oral products without antioxidants. In some cases, an oral product can include 0.01 and 5.00 weight percent antioxidant, between 0.05 and 1.0 weight percent antioxidant, between 0.10 and 0.75 weigh percent antioxidant, or between 0.15 and 0.5 weight percent antioxidant. Suitable examples of antioxidants include ascorbyl palmitate (a vitamin C ester), BHT, ascorbic acid (Vitamin C), and sodium ascorbate (Vitamin C salt). In some embodiments, monosterol citrate, tocopherols, propyl gallate, tertiary butylhydroquinone (TBHQ), butylated hydroxyanisole (BHA), Vitamin E, or a derivative thereof can be used as the antioxidant. For example, ascorbyl palmitate can be the antioxidant in some embodiments. Antioxidants can be incorporated into the polymer (e.g., polyurethane) during an extrusion process or after the polymer is extruded (e.g., during a post-extrusion flavoring process).

In some cases, the oral product 110 can have a conversion of less than 0.50% of nicotine into nicotine-N-oxide after aging the oral product 110 for 2 weeks at 25° C. and 65% relative humidity. In some cases, the oral product 110 can have a conversion of less than 0.20% of nicotine into nicotine-N-oxide after aging the oral product 110 for 2 weeks at 25° C. and 65% relative humidity. In some cases, the oral product 110 can have a conversion of less than 0.70% of nicotine into nicotine-N-oxide after aging the oral product 110 for 4 weeks at 25° C. and 65% relative humidity. In some cases, the oral product 110 can have a conversion of less than 0.30% of nicotine into nicotine-N-oxide after aging the oral product 110 for 4 weeks at 25° C. and 65% relative humidity. In some cases, the oral product 110 can have a conversion of less than 0.80% of nicotine into nicotine-N-oxide after aging the oral product 110 for 6 weeks at 25° C. and 65% relative humidity. In some cases, the oral product 110 can have a conversion of less than 0.40% of nicotine into nicotine-N-oxide after aging the oral product 110 for 6 weeks at 25° C. and 65% relative humidity. In some cases, the oral product 110 can have a conversion of less than 0.30% of nicotine into nicotine-N-oxide after aging the oral product 110 for 6 weeks at 25° C. and 65% relative humidity. In some cases, the oral product 110 can have a conversion of less than 0.85% of nicotine into nicotine-N-oxide after aging the oral product 110 for 8 weeks at 25° C. and 65% relative humidity. In some cases, the oral product 110 can have a conversion of less than 0.50% of nicotine into nicotine-N-oxide after aging the oral product 110 for 8 weeks at 25° C. and 65% relative humidity. In some cases, the oral product 110 can have a conversion of less than 0.85% of nicotine into nicotine-N-oxide after aging the oral product 110 for 10 weeks at 25° C. and 65% relative humidity. In some cases, the oral product 110 can have a conversion of less than 0.55% of nicotine into nicotine-N-oxide after aging the oral product 110 for 10 weeks at 25° C. and 65% relative humidity. In some cases, the oral product 110 can have a conversion of less than 0.95% of nicotine into nicotine-N-oxide after aging the oral product 110 for 12 weeks at 25° C. and 65% relative humidity. In some cases, the oral product 110 can have a conversion of less than 0.60% of nicotine into nicotine-N-oxide after aging the oral product 110 for 12 weeks at 25° C. and 65% relative humidity. In some cases, the oral product 110 can have a conversion of less than 1.07% of nicotine into nicotine-N-oxide after aging the oral product 110 for 30 weeks at 25° C. and 65% relative humidity. The presence of antioxidant can also reduce the formation of other tobacco derived impurities, such as Cotinine and myosime.

Sweeteners

A variety of synthetic and/or natural sweeteners can be used as additives in the oral product 110. Suitable natural sweeteners include sugars, for example, monosaccharides, disaccharides, and/or polysaccharide sugars, and/or mixtures of two or more sugars. According to some embodiments, the oral product 110 includes one or more of the following: sucrose or table sugar; honey or a mixture of low molecular weight sugars not including sucrose; glucose or grape sugar or corn sugar or dextrose; molasses; corn sweetener; corn syrup or glucose syrup; fructose or fruit sugar; lactose or milk sugar; maltose or malt sugar or maltobiose; sorghum syrup; mannitol or manna sugar; sorbitol or d-sorbite or d-sobitol; fruit juice concentrate; and/or mixtures or blends of one or more of these ingredients. The oral product 110 can also include non-nutritive sweeteners. Suitable non-nutritive sweeteners include: stevia, saccharin; Aspartame; sucralose; or acesulfame potassium.

Flavorants

The oral product 110 can optionally include one or more flavorants. The flavorants can be natural or artificial. For example, suitable flavorants include wintergreen, cherry and berry type flavorants, various liqueurs and liquors (such as Dramboui, bourbon, scotch, and whiskey) spearmint, peppermint, lavender, cinnamon, cardamon, apium graveolents, clove, cascarilla, nutmeg, sandalwood, bergamot, geranium, honey essence, rose oil, vanilla, lemon oil, orange oil, Japanese mint, cassia, caraway, cognac, jasmin, chamomile, menthol, ylang ylang, sage, fennel, pimenta, ginger, anise, coriander, coffee, liquorish, and mint oils from a species of the genus Mentha, and encapsulated flavors. Mint oils useful in particular embodiments of the oral product 110 include spearmint and peppermint. Synthetic flavorants can also be used. In certain embodiments, a combination of flavorants can be combined to imitate a tobacco flavor. The particular combination of flavorants can be selected from the flavorants that are generally recognized as safe ("GRAS") in a particular country, such as the United States. Flavorants can also be included in the oral product as encapsulated flavorants.

In some embodiments, the flavorants in the oral product 110 are limited to less than 20 weight percent in sum. In some embodiments, the flavorants in the oral product 110 are limited to be less than 10 weight percent in sum. For example, certain flavorants can be included in the oral product 110 in amounts of about 1 weight percent to 5 weight percent.

Other Additives

The oral product 110 may optionally include other additives. For example, these additives can include non-nicotine alkaloids, dietary minerals, vitamins, dietary supplements, therapeutic agents, and fillers.

Oral products 110 can also include vitamins, dietary minerals, other dietary supplements, and/or therapeutic agents. For example, suitable vitamins include vitamins A, B1, B2, B6, C, D2, D3, E, F, K, and P. For example, an oral product 110 can include C-vitamins with nicotine. Suitable dietary minerals include calcium (as carbonate, citrate, etc.) or magnesium (as oxide, etc.), chromium (usually as picolinate), and iron (as bis-glycinate). One or more dietary minerals could be included in an oral product with or without the use of other additives. Other dietary supplements and/or therapeutic agents can also be included as additives.

In some embodiments, the oral product 110 includes a therapeutic agent that is preferable absorbed transbuccally. For example, so therapeutic agents do not pass into the blood stream if they are swallowed. Exemplary therapeutic agents that can be included in an oral product 110 provided herein can include Gerd, Buprenorphin, Nitroglycerin, Diclofenac, Fentanyl, Carbamazepine, Galantamine, Acyclovir, Polyamidoamine Nanoparticles, Chlorpheniramine, Testosterone, Estradiol, Progesterone, Calcitonin, Fluorouracil, Naltrexone, Odansetron, Decitabine, Selegiline, Lamotrigine, and Prochlorperazine. For example, an oral product 110 can include Buprenorphine and be used for pain treatment. In some embodiments, an oral product 110 can include Nitroglycerin and be used for Angina Pectoris treatment. Because of the release properties of the oral product 110, therapeutic agents included therein can be released at a rate such that a majority of the therapeutic agent is absorbed transbuccally, rather than swallowed.

The oral product 110 can also include fillers such as starch, di-calcium phosphate, lactose, sorbitol, mannitol, and microcrystalline cellulose, calcium carbonate, dicalcium phosphate, calcium sulfate, clays, silica, glass particles, sodium lauryl sulfate (SLS), glyceryl palmitostearate, sodium benzoate, sodium stearyl fumarate, talc, and stearates (e.g., Mg or K), and waxes (e.g., glycerol monostearate, propylene glycol monostearate, and acetylated monoglycerides), stabilizers (e.g., ascorbic acid and monosterol citrate, BHT, or BHA), disintegrating agents (e.g., starch, sodium starch glycolate, cross caramellose, cross linked PVP), pH stabilizers, or preservatives. In some embodiments, the amount of filler in the oral product 110 is limited to less than 10 weight percent in sum. In some embodiments, the amount of filler in the oral product 110 is limited to be less than 5 weight percent in sum. In some embodiments, the fillers are mouth stable. In other embodiments, the fillers can dissolve or disintegrate during use and thus result in an oral product that becomes more pliable during use.

In some embodiments, the oral product 110 can include nicotine as an additive (optionally with additional sweeteners and flavors) and non-tobacco cellulosic fiber, and thus be substantially free of tobacco plant tissue.

Plasticizers

The oral product 110 can also include one or more plasticizers. Plasticizers can soften the final oral product and thus increase its flexibility. Plasticizers work by embedding themselves between the chains of polymers, spacing them apart (increasing the "free volume"), and thus significantly lowering the glass transition temperature for the plastic and making it softer. Suitable plasticizers include propylene glycol, glycerin, vegetable oil, and medium chain triglycerides. In some embodiments, the plasticizer can include phthalates. Esters of polycarboxylic acids with linear or branched aliphatic alcohols of moderate chain length can also be used as plasticizers. Moreover, plasticizers can facilitate the extrusion processes described below. In some embodiments, the oral product 110 can include up to 20 weight percent plasticizer. In some embodiments, the oral product 110 includes between 0.5 and 10 weight percent plasticizer, the oral product 110 can include between 1 and 8 weight percent plasticizer, or between 2 and 4 weight percent plasticizer. For example, an oral product comprising a polyurethane polymer matrix and include about 3 to 6.5 weight percent of propylene glycol.

Molding Processes

The oral product 110 can be produced by extruding a mouth-stable polymer (e.g., polyurethane) with fibers (e.g., cellulosic fiber) and/or additive (e.g., nicotine) to form a rod of a mouth-stable polymer matrix including fibers and/or additives. The rod is cut into individual oral products 110.

For example, a mouth-stable polymer (e.g., polyurethane) can be introduced into an extruder for extrusion along with cellulosic fibers and one or more mouth-soluble binders. For example, the mouth-soluble binders can include guar gum, xanthan, cellulose gum, or a combination thereof. The mouth-soluble binders can either be pre-mixed with the cellulosic fibers or added separately into the extruder. The cellulosic fibers can be passed through a sieve prior to introduction into the extruder. A mixture of additives can also be introduced into the extruder. The mixture of additives can be a solution. The additives can include a plasticizer (e.g., propylene glycol) and a sweetener (e.g., sucralose). The mixture of additives can also be provided in slurry form or a dry mix of powdered additives.

The polymer-fiber-binder combination can exit an extrusion die as a rod and onto a moving conveyor. The size of the extrusion die, the take away speed of the moving conveyor, the mixture of polymer-fiber-binder combination, and the temperature of the mixture exiting the die can all have an impact on the final diameter of the rod.

The extruded polymer-fiber rod can then cut in a cutting process.

In addition to the methods described above, there are many methods for making and shaping the oral products. In some embodiments, extruded and cut pieces can be introduced into a compression mold to form a final oral product shape. In other embodiments, the oral product 110 can be injection molded, compression molded, or injection-compression molded. Blocks of polymer, fiber, and/or additive can also be formed and machined into a desired shape.

EXAMPLES

A series of oral products were produced by combining polyurethane, cellulosic fiber, -xanthan gum, guar gum, cellulose gum, nicotine, ascorbyl palmitate antioxidant, maltodextrin soluble fibers, propylene glycol, sweeteners, and flavorants to produce a variety of oral products. The oral products were made by pre-blending certain ingredients, extruding at least some of the ingredients together to form a rod, cutting the rod into oral products, and flavoring the oral products. A first pre-blended mixture was formed to include cellulose fiber, maltodextrin soluble fiber, xanthan gum, guar gum and cellulose gum. A second mixture include additional ingredients was also created. Polyurethane, the pre-blended mixture, and the second mixture were each metered into the extruder at a controlled feed rate, to form an extruded rod. The extruded rod was cut and subsequently flavored. The pre-blended mixture formed about 20-50 weight percent of the formed oral products. The formed oral products included between 40 weight percent and 85 weight percent polyurethane. The formed oral products included between 1 weight percent and 25 weight percent of the second mixture.

Product samples were cut to have a thickness of about 3 mm and subjected to the compression @ 250 N test, the compression @ 425 N test, and the springiness test discussed above. The oral products had a compression @250N ranging from 83% to 88%; a compression @425N ranging from 97% to 99%; and a springiness ranging from 85% to 89%.

A series of oral products were also tested in a mastication test to determine the additive release profile. Each sample was placed in a mastication tester that manipulated the sample in a solution that mimics saliva. At varying time intervals, samples were taken from the mastication tester to determine the total amount of menthol and nicotine released. The results of this mastication test are shown in Table I below.

TABLE I

Average (n = 2) Relative Cumulative Concentration (mg/Piece)

|  | Time (min) | Nicotine | STDEV |
|---|---|---|---|
| V-031513-S4-1 | 5 | 0.31 | 0.01 |
| V-031513-S4-2 | 10 | 0.50 | 0.06 |
| V-031513-S4-3 | 15 | 0.67 | 0.07 |
| V-031513-S4-4 | 30 | 0.89 | 0.10 |
| V-031513-S4-5 | 45 | 1.08 | 0.12 |
| V-031513-S4-6 | 60 | 1.19 | 0.04 |
|  | Time (min) | Methanol | STDEV |
| V-031513-S4-1 | 5 | 0.18 | 0.02 |
| V-031513-S4-2 | 10 | 0.33 | 0.00 |
| V-031513-S4-3 | 15 | 0.45 | 0.02 |
| V-031513-S4-4 | 30 | 0.53 | 0.02 |
| V-031513-S4-5 | 45 | 0.67 | 0.01 |
| V-031513-S4-6 | 60 | 0.73 | 0.03 |

OTHER EMBODIMENTS

It is to be understood that, while the invention has been described herein in conjunction with a number of different aspects, the foregoing description of the various aspects is intended to illustrate and not limit the scope of the invention, which is defined by the scope of the appended claims. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. An oral product comprising:
a mouth-stable polymer in an amount of 40 weight percent to 80 weight percent;
a cellulosic material in an amount of greater than or equal to 10 weight percent;
a mouth-soluble binder in an amount of 0.1 weight percent to 5 weight percent;
triglycerides in an amount of less than or equal to 20 weight percent; and
nicotine or a nicotine derivative, the oral product having a springiness of greater than or equal to 20 weight percent.

2. The oral product of claim 1, wherein the triglycerides include medium chain triglycerides.

3. The oral product of claim 1, wherein the mouth-stable polymer includes a single polymer.

4. The oral product of claim 1, wherein the mouth-stable polymer includes a blend of polymers.

5. The oral product of claim 1, wherein the mouth-stable polymer includes polyurethane, silicon polymer, polyester, polyacrylate, polyethylene, poly(styrene-ethylene-butylene-styrene), poly(styrene-butadiene-styrene), poly(styrene-isoprene-styrene), any copolymer thereof, or any combination thereof.

6. The oral product of claim 1, wherein the mouth-stable polymer includes polyurethane.

7. The oral product of claim 1, wherein the cellulosic material includes microcrystalline cellulose.

8. The oral product of claim 1, wherein the cellulosic material includes sugar beet fibers, wood pulp fibers, cotton fibers, bran fibers, citrus pulp fibers, grass fibers, willow fibers, poplar fibers, or any combination thereof.

9. The oral product of claim 1, wherein the mouth-soluble binder includes carboxymethyl cellulose, hydroxypropyl cellulose, hydroxyethyl cellulose, hydroxypropyl methyl cellulose, methyl cellulose, starch, modified starch, konjac, collagen, inulin, soy protein, whey protein, casein, and wheat gluten, carrageenan, alginates, xanthan, dextrin, pullulan, curdlan, gellan, locust bean gum, guar gum, tara gum, gum tragacanth, pectin, agar, zein, karaya, gelatin, *psyllium* seed, chitin, chitosan, gum acacia, shellac, polyvinyl pyrrolidone, polyethylene oxide, polyvinyl alcohol, or any combination thereof.

10. The oral product of claim 1, wherein the mouth-soluble binder includes guar gum, xanthan, cellulose, or any combination thereof.

11. The oral product of claim 1, further comprising:
a sweetener.

12. The oral product of claim 11, wherein the sweetener comprises saccharine, sucralose, aspartame, acesulfame potassium, isomaltulose, a sub-combination thereof, or a combination thereof.

13. The oral product of claim 1, wherein the nicotine or the nicotine derivative includes tobacco-derived nicotine.

14. The oral product of claim 1, wherein the oral product defines a plurality of pores.

15. The oral product of claim 14, wherein the plurality of pores includes,
a first portion having a first diameter, and
a second portion having a second diameter, the second diameter different from the first diameter.

16. The oral product of claim 15, wherein
the first diameter ranges from 40 microns to 60 microns, and
the second diameter ranges from 1 micron to 10 microns.

17. The oral product of claim 1, further comprising
an antioxidant.

18. The oral product of claim 1, further comprising:
soluble fibers.

19. The oral product of claim 18, wherein the soluble fibers include maltodextrin.

20. The oral product of claim 1, wherein
the springiness ranges from 75% to 95%,
the oral product has a compressibility at 250 N ranging from 45% to 95%, and
the oral product has a compressibility at 425 N ranging from 60% to 98%.

\* \* \* \* \*